(12) United States Patent
Becker et al.

(10) Patent No.: US 8,468,642 B2
(45) Date of Patent: Jun. 25, 2013

(54) WINDOW SCRAPER FOR AN OPTICAL INSTRUMENT

(75) Inventors: Richard Becker, Carnation, WA (US); Craig J. Cornelius, Woodinville, WA (US); Oliver Hamann, Sammamish, WA (US); Evandro Mendonca, Redmond, WA (US); Robert E. LaVigueur, Anchorage, AK (US)

(73) Assignee: Mettler-Toledo Autochem, Inc., Columbia, MD (US)

( * ) Notice: Subject to any disclaimer, the term of this patent is extended or adjusted under 35 U.S.C. 154(b) by 987 days.

(21) Appl. No.: 12/404,021

(22) Filed: Mar. 13, 2009

(65) Prior Publication Data
US 2009/0229067 A1 Sep. 17, 2009

Related U.S. Application Data

(60) Provisional application No. 61/036,333, filed on Mar. 13, 2008.

(51) Int. Cl.
*A47L 1/00* (2006.01)
(52) U.S. Cl.
USPC ... 15/250.361; 356/335; 356/256; 15/250.48; 15/250.001; 15/250.32
(58) Field of Classification Search
USPC .............. 15/97.1, 103, 250.001, 250.002, 15/250.003, 250.13, 250.14, 250.19, 250.202, 15/250.22, 250.29, 250.3, 250.31, 250.4, 15/250.41, 250.32; 356/335, 336, 337, 338, 356/339, 340, 341, 342, 343
See application file for complete search history.

(56) References Cited

U.S. PATENT DOCUMENTS

| | | | | |
|---|---|---|---|---|
| 1,938,840 A * | 12/1933 | Kleven | .................. | 15/250.32 |
| 2,582,717 A * | 1/1952 | Pierce | .................. | 15/250.04 |
| 2,707,298 A | 5/1955 | Wiest, Jr. | | |
| 2,727,270 A * | 12/1955 | Bosso | .................. | 15/250.43 |
| 3,837,036 A * | 9/1974 | Burger et al. | .................. | 15/250.23 |
| 3,844,661 A | 10/1974 | Birkett | | |
| 4,422,206 A * | 12/1983 | Brace et al. | .................. | 15/236.02 |
| 4,719,661 A * | 1/1988 | Hanselmann | .................. | 15/250.203 |
| 5,185,531 A | 2/1993 | Wynn | | |
| 5,208,938 A * | 5/1993 | Webb | .................. | 15/250.22 |
| 5,983,504 A * | 11/1999 | Tisbo et al. | .................. | 30/164.5 |
| 2002/0139394 A1 | 10/2002 | Bronson | | |
| 2003/0233723 A1 | 12/2003 | Lizotte | | |
| 2006/0199998 A1 | 9/2006 | Akui | | |
| 2007/0002319 A1 | 1/2007 | Knopp | | |
| 2008/0212101 A1* | 9/2008 | Wolf et al. | .................. | 356/445 |

FOREIGN PATENT DOCUMENTS

DE  29508980 U1 * 9/1996
EP  1 541 995 A1  6/2005

(Continued)

OTHER PUBLICATIONS

International Search Report and Written Opinion of the International Searching Authority mailed Jun. 3, 2009, in corresponding International Application No. PCT/US2009/037159, filed Mar. 13, 2009.

*Primary Examiner* — Joseph J Hail
*Assistant Examiner* — Henry Hong
(74) *Attorney, Agent, or Firm* — Standley Law Group LLP (57) ABSTRACT

A scraper for an optical surface of a device is disclosed. The scraper includes a blade having an edge that is rigid and non-deforming to withstand high shear stresses. The blade is configured to rotate about a first axis parallel to the optical surface and also configured to move in a line with respect to a second axis perpendicular to the optical surface. This allows the rigid, non-deforming blade to maintain contact with the optical surface. Furthermore, the edge is configured to move across the optical surface to remove any materials adhered to the surface. The scraper can be used to clean the optical surface of an instrument, for example.

19 Claims, 5 Drawing Sheets

FOREIGN PATENT DOCUMENTS

| | | |
|---|---|---|
| GB | 489352 A | 7/1938 |
| JP | 5-45273 A | 2/1993 |
| JP | 8-248370 A | 9/1996 |
| JP | 2001-205072 A | 7/2001 |
| JP | 2002-88562 A | 3/2002 |
| JP | 2004-230315 A | 8/2004 |
| JP | 2007-117103 A | 5/2007 |
| MX | PA04009013 A | 11/2004 |
| WO | 96/12938 A1 | 5/1996 |
| WO | 03/078975 A3 | 9/2003 |
| WO | 2007/012878 A1 | 2/2007 |
| WO | 2007/090717 A1 | 8/2007 |

* cited by examiner

WINDOW SCRAPER FOR AN OPTICAL INSTRUMENT

CROSS-REFERENCE TO RELATED APPLICATION

This application claims the benefit of Provisional Application No. 61/036,333, filed Mar. 13, 2008, which application is incorporated herein by reference in its entirety.

BACKGROUND

Optical instruments, such as, but not limited to, particle size characterization scanners, which operate in crystallization or granulation processes that experience particle growth, often have their optical performance degraded by the deposition of particles on their external windows. Such depositions are often so rigidly attached to the windows that squeegee and brush-type wipers cannot dislodge the particles from the windows.

Accordingly, alternatives are desired to overcome the problems with the conventional brush-type wipers and squeegees.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A scraper for an optical surface of a device is disclosed. The scraper includes a blade having an edge that is rigid and non-deforming to withstand high shear stresses. The blade is configured to rotate about a first axis parallel to the optical surface and also configured to move in a line with respect to a second axis perpendicular to the optical surface. This allows the rigid, non-deforming blade to maintain contact with the optical surface. Furthermore, the edge is configured to move across the optical surface to remove any materials adhered to the surface. The scraper can be used to clean the optical surface of an instrument, for example.

The edge is configured to have three degrees of freedom of movement in order to maintain contact with the optical surface and to remove materials or particles present on the optical surface.

One degree of freedom of movement is the ability of the blade to rotate about a first axis that is parallel to the optical surface so that the edge can make contact with the surface when the optical surface is skewed with respect to the axis. The pivot point of rotation lies on the edge of the blade.

One degree of freedom of movement is forwards and backwards with respect to the optical surface, wherein the scraper blade is biased or pressed against the optical surface so that the edge can make contact with the optical surface when the optical surface is skewed with respect to a second axis parallel to the optical surface and perpendicular to the first axis.

One degree of freedom of movement is across the optical surface, which can be rotation or translation across the optical surface, and oscillatory.

One embodiment for allowing the blade to rotate to keep contact with the optical surface when the surface is skewed with respect to an axis parallel to the optical surface includes placing the blade within a slot that includes a curved surface such that the proximal side of the blade includes a matching curved surface to allow rotation in the slot.

The blade may include a plurality of scraping edges, wherein each scraping edge is made up of two adjoining surfaces coming together to form an angle of 90 degrees or less. The scraper blade may have two edges to allow scraping in a forward and backward direction.

A pivot shaft is attached to a driver at one end thereof. The pivot shaft is connected to a bracket on the opposite end thereof. The pivot shaft is configured so as to apply a force such that the scraper blade is pressed against the optical surface to produce high shear stresses on any material that accumulates on the surface. The pivot shaft allows the second degree of freedom of movement to allow the blade to move forwards and backwards in a direction perpendicular to the optical surface to allow contact with the optical surface when the optical surface is skewed with respect to a vertical axis.

The scraper blade edge may be made from a metal, ceramic, or plastics. The scraper blade edge is less hard than the optical surface to avoid scratching of the surface.

Because the scraper blade edge is rigid and, therefore, cannot bend or conform to maintain contact with the flat surface of the optical surface to operate as desired, the scraper blade has three degrees of freedom. First, the blade rotates along an axis parallel to the optical surface such that the blade edge can align itself to the surface. Second, the scraper blade is also able to translate forwards and backwards in line with an axis perpendicular to the optical surface, i.e., in towards the optical surface or away from the optical surface. Third, the scraper blade can move across the optical surface, such as by rotation or translation across the surface.

A bracket that connects the shaft to the blade can have a slot for insertion of the blade. The slot includes a curved surface against which the proximal side of the blade seats and the proximal side of the blade include a matching curved surface. This permits the scraper blade to rotate about the center of a pivot point that is parallel to the optical surface, i.e., the pivot point lies along the edge of the blade.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Embodiments of the present invention are related to scrapers for windows, including, but not limited to, the process side optical surface of windows. As used herein, optical surfaces are present in, but are not necessarily limited to, optical instruments.

A window can be any surface that collects, attracts, or on which particles or other materials of any kind accumulate. For example, applications in which embodiments of the disclosed window scraper may be used include particle processing, such as in the area of pharmaceuticals manufacturing, where binders, such as cellulose and lactose, can accumulate on instruments. However, other applications for the disclosed window scraper are possible, such as, but not limited to any instrument, sensor, device, and surface used in chemical processing and manufacturing, and other fields. In general, any application requiring the removal of particles and/or materials from a surface are suitable applications in which the disclosed window scraper may be used. Although the following description of a representative window scraper is with reference to an optical instrument, the window scraper is not thereby limited solely for use in this application.

Figure 1:
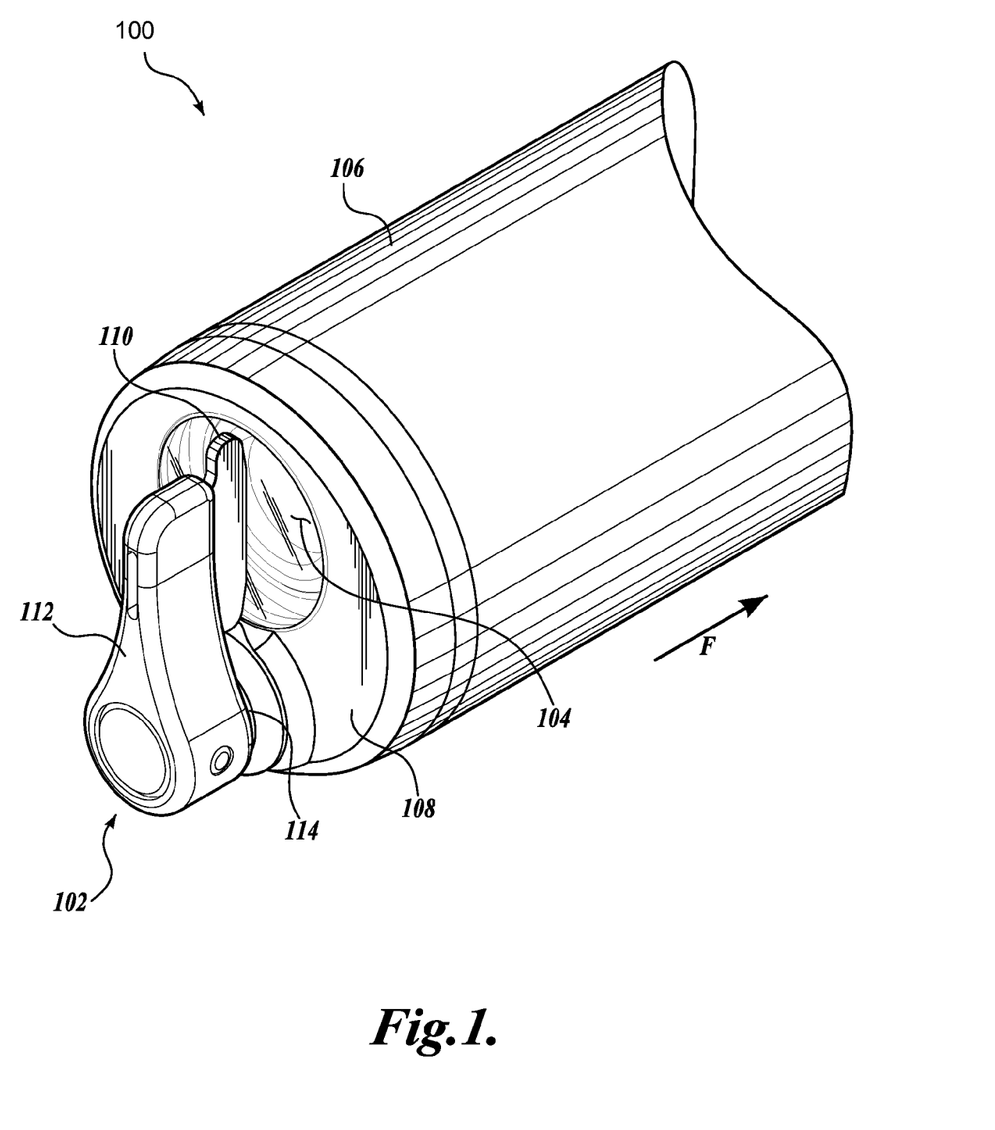
FIG. 1 is a diagrammatical illustration of an optical instrument and a window scraper in accordance with one embodiment of the present invention.
Figure 2:
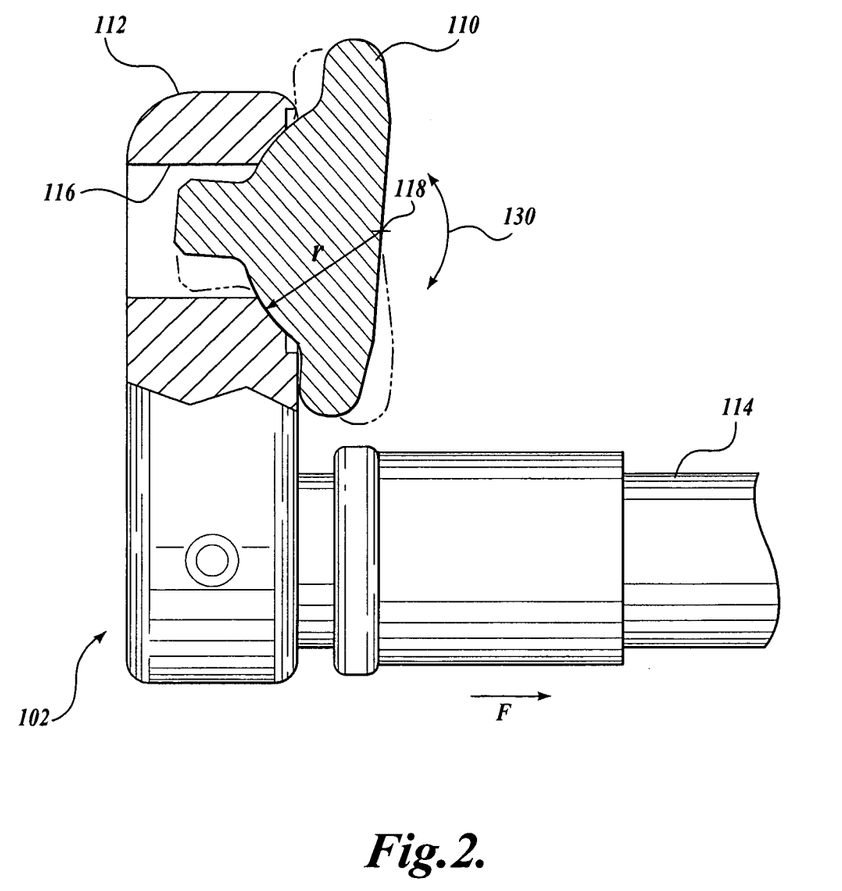
FIG. 2 is a diagrammatical illustration of a cross-sectional view of a window scraper in accordance with one embodiment of the present invention.

Referring collectively to both FIGS. 1 and 2, a representative optical instrument 100 is illustrated. The specific details of the optical instrument 100 are not disclosed herein for brevity. In one particular embodiment, the optical instrument 100 includes an elongated tube 106. The elongated tube 106 includes a distal end 108. The distal end 108 of instrument 100 includes a window 104. The window 104 has an optical surface on the distal side thereof. The distal end 108 of instrument 100 may be positioned within any location having a material or condition that is desired to be measured by the instrument 100. For example, the distal end 108 of instrument 100 can be inserted in any pipeline, vessel, tank, reactor, and the like. In one particular embodiment, the instrument 100 is a particle characterization instrument that can measure any one or more of the size, shape, chemical composition, and concentration of particles. An "optical surface" as used herein, refers to any material through which electromagnetic radiation may be transmitted. Electromagnetic radiation includes visible light, near infrared, middle infrared, and far infrared radiation, for example. However, embodiments of the optical surface should not be construed as being limited to any particular wavelength of electromagnetic radiation.

Optical surfaces out of which the window 104 can be made can include, but are not limited to the following materials: industrial sapphire (aluminum dioxide crystals), industrial diamond, glass, quartz, fusila, surface-hardened materials, diamond-coated materials, nano-coated materials, silicon, and the like. A common characteristic of the above-mentioned materials is the ability to transmit a form of electromagnetic radiation that may be emitted or received by the instrument 100.

The instrument 100 includes a window scraper 102. The window scraper 102 includes a pivot shaft 114, a blade bracket 112 connected to the distal end of the pivot shaft 114, and a scraper blade 110 connected to the end of the blade bracket 112. The pivot shaft 114 extends parallel to the longitudinal axis of the instrument 100 and can be internal to the elongated tube 106 of the instrument 100. The proximal end of the pivot shaft 114, which is not shown in FIGS. 1 and 2, is understood to be connected to a drive mechanism. The drive mechanism may impart an oscillatory motion to the pivot shaft 114. The blade bracket 112 is attached at the distal end of the pivot shaft 114 perpendicular to the axis of rotation of the pivot shaft 114. The blade bracket 112 includes a lower end and an upper end. The lower end is attached to the distal end of the pivot shaft 114. The upper end of the blade bracket 112 includes a blade slot 116. The blade slot 116 supports the scraper blade 110. The scraper blade 110 is allowed to rotate in the blade slot 116 about the blade pivot 118 as indicated by the double-headed arrow 130 in FIG. 2. The pivot shaft 114 exerts a force in the direction of the arrow with the designation "F." Thus, the pivot shaft 114 forces the scraper blade 110 against the window 104 surface to produce high shear stresses on any material accumulated on the surface of window 104 caused by the movement of the scraper blade 110, thus effectively removing such accumulated material The scraper blade 110 or, at the very least, the portion of the scraper blade 110 (i.e., the edge) that contacts the window 104 is made of a material that is rigid and is generally non-deformable during scraping. Suitable materials for the scraper blade 110 edge include, but are not limited to, metals, ceramics, rigid plastics, and the like. The scraper blade 110 edge is less hard than the window 104 surface material to prevent scratching of the window 104 surface. The scraper blade 110 edge advantageously withstands high shear forces required to dislodge particle deposits. The scraper blade 110 edge is advantageously hard enough such that the abrasion associated with scraping does not substantially wear the scraping edges of the scraper blade 110 too quickly. Preferably, the scraper blade 110 edge is also corrosion resistant to some degree. One representative material for a scraper blade 110 includes stainless steel, such as 13-8 stainless hardened to RC35, for example. The scraper blade 110 edge is rigid and, therefore, cannot bend or conform to maintain contact with a flat surface of the window 104. To operate as desired, the scraper blade 110 has three degrees of freedom. For the scraping action to occur, the scraper blade 110 is able to rotate about an axis perpendicular to the window, or, in other embodiments, the scraper blade 110 can be configured to translate along an axis parallel to the window 104 and perpendicular to the scraping edges. In the illustrated embodiment, the scraper blade 110 lies vertically and is rotated by the pivot shaft 114. To keep the scraping edge or edges parallel to the window 104, the scraper blade 110 is able to rotate about an axis parallel and horizontal to the window 104 and perpendicular to the scraping edges, i.e., about the blade pivot 118 as shown in FIG. 2. This keeps the blade 110 in contact with the window if the window is skewed with respect to a horizontal axis. The scraper blade 110 is also able to translate either forwards or backwards or in line along an axis perpendicular to the window 104 to keep the blade in contact with the window 104, i.e., in the direction of the force F. This keeps the blade 110 in contact with the window when the window is skewed with respect to a vertical axis. In other embodiments, for example, when the scraper is positioned to the side of the window 104, the blade 110 will then lie horizontally and would be configured to rotate about an axis that is parallel and vertical to the window 104. In this case, the rotation of the blade along this vertical axis allows for the blade to keep in contact with the window, when the window is skewed with respect to the vertical axis. The blade would also be configured to move in line with an axis that is perpendicular to the surface. The force being exerted on the blade to press against the window in the forward direction allows the blade to keep in contact with the window, when the window is skewed with respect to a horizontal axis. Therefore, two degrees of freedom of movement that include rotation of the blade about a pivot point parallel to the optical surface, and movement in a direction that is in line with an axis that is perpendicular to the optical surface, such as forwards and backwards, are needed to keep the blade in contact with the optical surface. The third degree of movement provides for the blade to move across the surface.

Besides using a straight blade edge, the blade edge can be arcuate, concave, or convex to match the shape of the optical surface.

In a preferred embodiment, the scraper blade 110 is able to rotate about the blade pivot 118, the scraper blade 110 is fitted into the slot 116 in the blade bracket 112. The slot 116 is perpendicular to the window 104 and parallel to the axis of the pivot shaft 114. The back edge of the scraper blade 110 and the front side of the slot 116 may have a matching radius that permits the scraper blade 110 to rotate about the center of that radius at the blade pivot 118. This rotation allows the scraping edge or edges to align themselves parallel to the window 104. Additionally, the center of the scraper blade 110 rotation is located at the window 104 surface. This results in minimum coupling between scraper blade 110 rotation and the slot 116 and scraper blade 110 translation along the pivot shaft 114. This also minimizes the force required to keep the scraping edges parallel to the window 104. While this arrangement of the blade pivot is advantageous any other arrangements, including mechanical pivot axes, flexure mounts and the like that allow a pivoting motion around an axis essentially parallel to the window surface and collinear with the direction of the motion of the wiper blade may be suitable.

Figure 3:
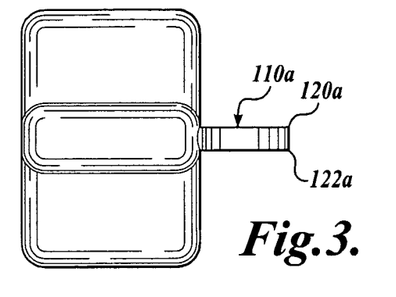
FIG. 3 is a diagrammatical illustration of a top view of a portion of a scraper blade in accordance with one embodiment of the present invention.

In one embodiment, the scraper blade 110 has a width and a length significantly greater than its thickness. The plane formed by the length and width is oriented perpendicular to the window 104 surface. The thin distal face of the scraper blade 110 makes contact with the window 104. FIG. 3 is a diagrammatical illustration of a portion of the top view of the scraper blade 110 showing the configuration of the thin face. The scraping edges of the scraper blade 110 are represented in FIG. 3 as reference numerals 120a and 122a. The scraping edges 120a and 122a that are formed on the thin face of the scraper blade 110 are perpendicular to the direction of scraping and are sharp. FIG. 3 illustrates two scraping edges 120a and 122a, so that scraping action is performed on both the forward and backward phases of oscillatory motion.

Figure 4:
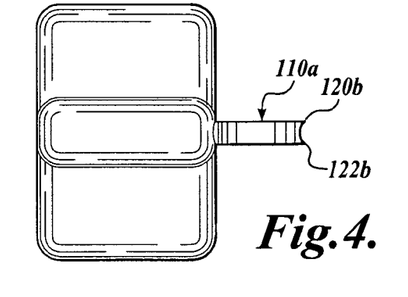
FIG. 4 is a diagrammatical illustration of a top view of a portion of a scraper blade in accordance with one embodiment of the present invention.
Figure 5:
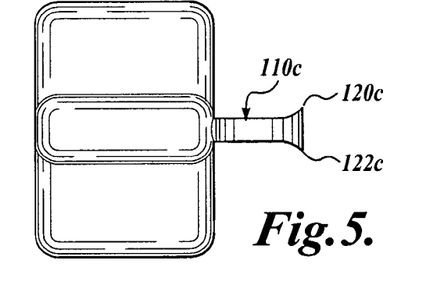
FIG. 5 is a diagrammatical illustration of a top view of a portion of a scraper blade in accordance with one embodiment of the present invention.
Figure 6:
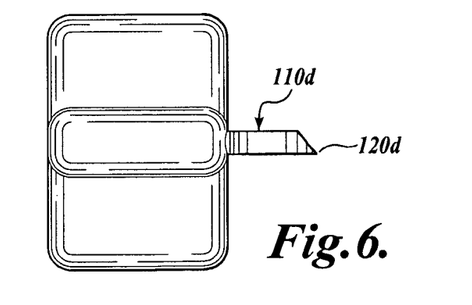
FIG. 6 is a diagrammatical illustration of a top view of a portion of a scraper blade in accordance with one embodiment of the present invention.
Figure 7:
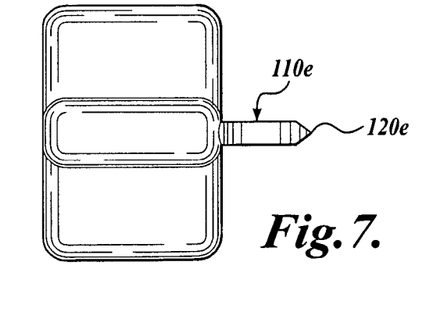
FIG. 7 is a diagrammatical illustration of a top view of a portion of a scraper blade in accordance with one embodiment of the present invention.

Other embodiments of sharp scraping edges are illustrated in FIGS. 4, 5, 6, and 7. FIGS. 4 and 5 illustrate two sharp scraping edges 120b, 122b, 120c, and 122c at the face of the scraper blade, whereas FIGS. 6 and 7 illustrate a single sharp scraping edge 120d and 120e. The scraping edge of FIGS. 6 and 7 may be used on a scraper blade that travels in a single direction. The scraping edges illustrated in FIGS. 3, 4, and 5 may also be used on a window scraper 102 traveling in a single direction; however, when one scraping edge is determined to be dull or not performing, such as by noticing reduced light transmissivity, the window scraper 102 may automatically reverse direction to use the second scraping edge. Generally, the scraping edges illustrated in FIGS. 3 to 7 are formed by two adjoining surfaces making an angle of 90 degrees or less.

Figure 8:
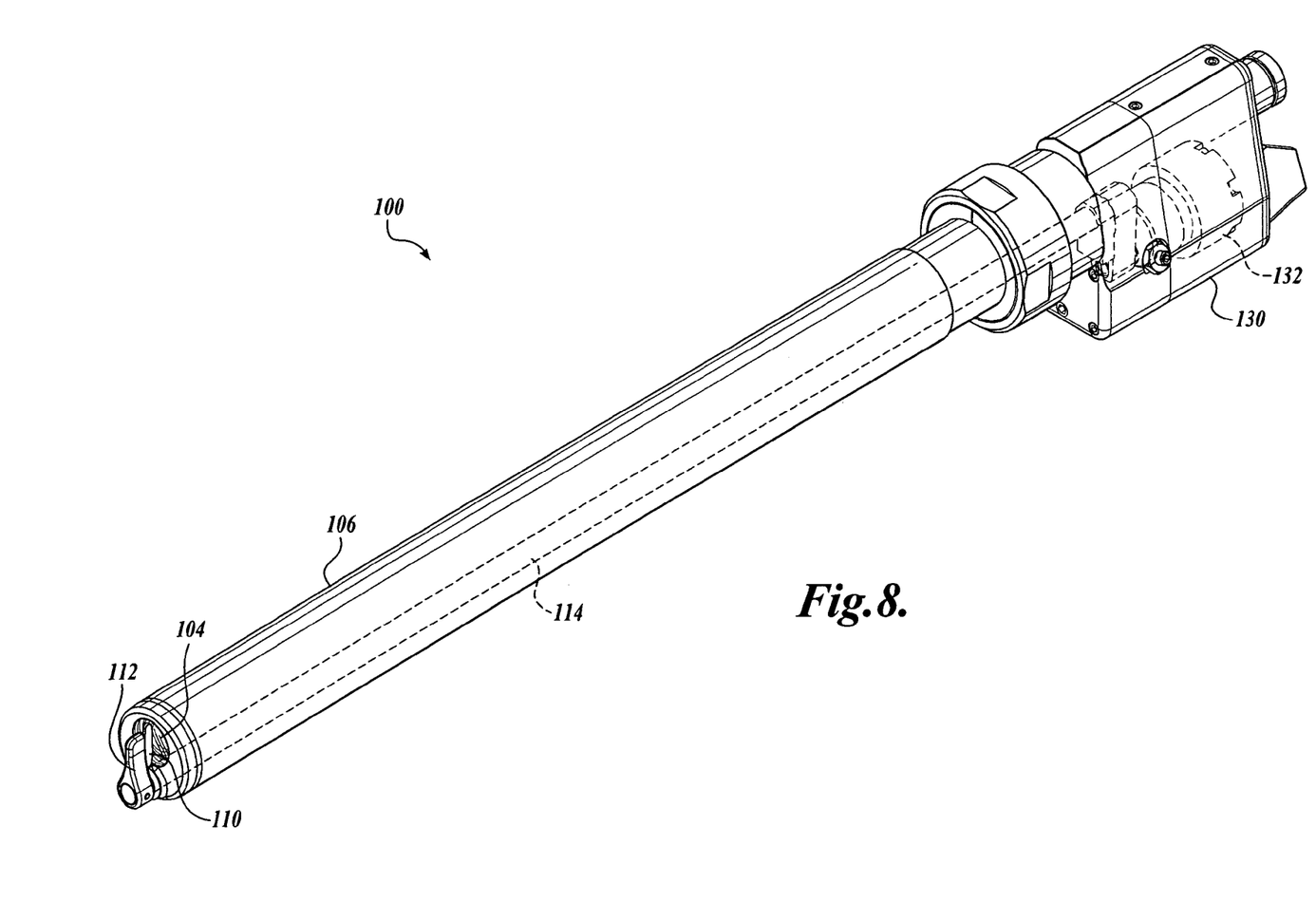
FIG. 8 is a diagrammatical illustration of an instrument and window scraper in accordance with one embodiment of the present invention.
Figure 9:
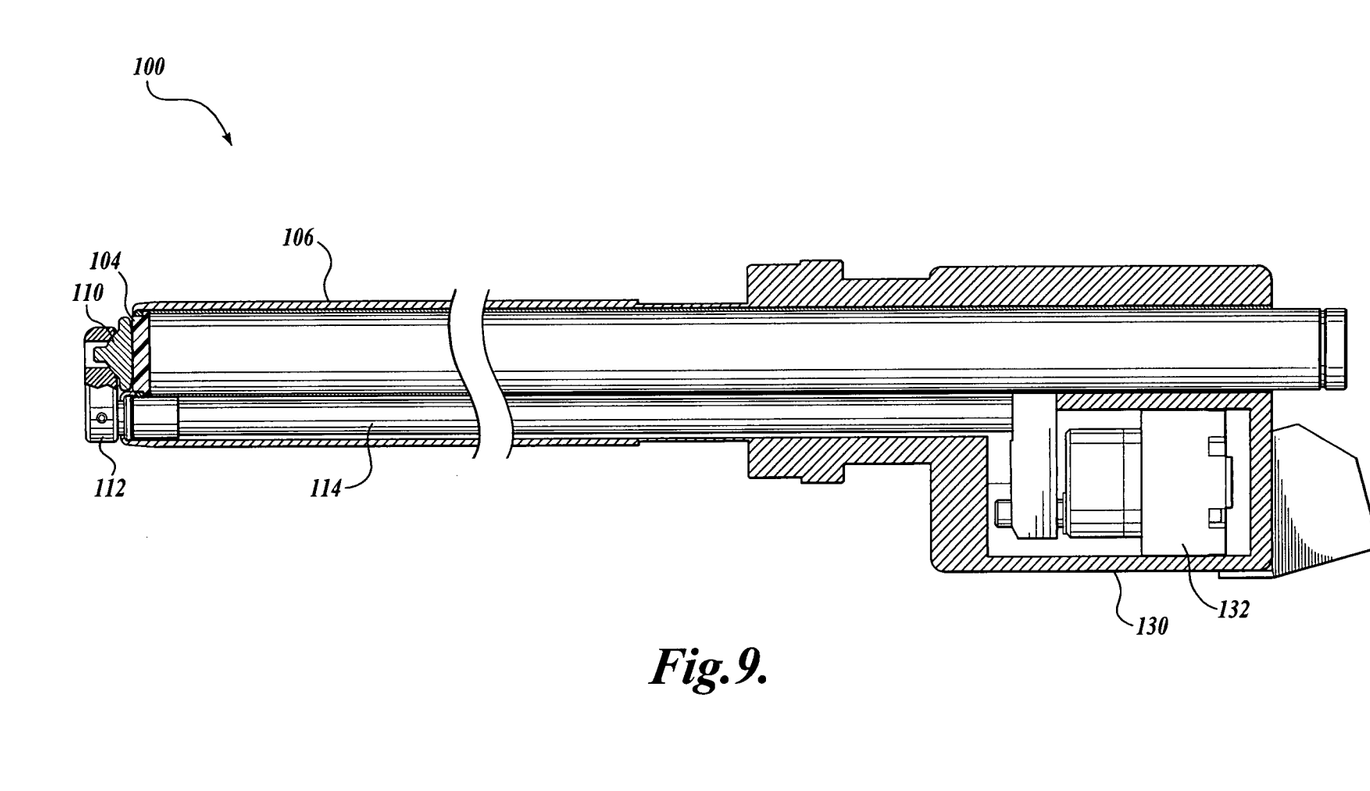
FIG. 9 is a diagrammatical illustration of a cross-sectional view of an instrument and window scraper in accordance with one embodiment of the present invention.

FIGS. 8 and 9 are diagrammatical illustrations of the entire instrument 100 and window scraper. As mentioned above, the design and type of instrument does not affect the window scraper of the invention, but is merely shown to illustrate one representative embodiment of how the window scraper may be used. The complete window scraper is shown, including the pivot shaft 114 that is attached at the proximal end to a driver 132 within a housing 130. The driver 132 can impart an oscillatory motion to the pivot shaft that in turn moves the bracket 112 and blade 110 across the surface of the window 104. The pivot shaft is also configured to move in the direction either forwards or backwards perpendicular to the window 104, thus allowing the blade 110 to maintain contact with the window 104. To this end, the pivot shaft 114 is fitted with appropriate bearings to support rotation as well as in line movement of the shaft. The pivot shaft can be biased forwards, such as with a spring, so that the blade 110 exerts pressure on the window 104 surface.

Although one representative embodiment of a window scraper 102 has been illustrated and described, it is to be appreciated that variations are encompassed within the scope of this disclosure. A window scraper 102, as disclosed herein, is suitable to be used on or in connection with a surface, optical or otherwise, that is desired to be cleansed of adhering particles and/or materials. Furthermore, the motion of the scraper blade 110 in relation to the window 104 to be scraped can take any one of various implementations. The scraper blade 110 may be rotated through a sector of an arc in an oscillatory motion. Alternatively, the scraper blade 110 may be attached to a guide or rail that causes the scraper blade 110 to translate in a straight line across the window 104 surface, again in an oscillatory motion. As another alternative, the scraper blade 110 can be attached to a pivot shaft wherein the pivot shaft rotates in a continuous or periodic fashion making a complete 360 degree rotation. Furthermore, more than one scraper blade 110 can be provided on a single blade bracket 112, or, alternatively, multiple blade brackets 112 may be provided with a single scraper blade 112 on each blade bracket 112. For that matter, the scraper blade 110 can be configured to scrape more than one window. Numerous other modifications are readily apparent from the above disclosure.

In other embodiments, the operation of the window scraper 102 can be controlled by a means for indicating when the window 104 needs to be scraped. For example, by measuring the light transmissivity through the window 104 with a sensor, a predetermined limit can be set that actuates the window scraper 102 to remove the adhered materials, thus restoring the light transmissivity to the normal operating range. Should the window scraper 102 be used for an optical instrument with measurement capability, means can be provided that indicate when the window scraper 102 is in operation that causes the measurement readings from the optical instrument to be discarded or disregarded as accurate readings. Means can also be provided when the scraping operation is completed, thus indicating that instrument measurement readings are once again indicating accurate operating conditions. Means to determine when the window scraper 102 is in operation as a cut-off means for measuring instrument readings can include a position sensor, a motion sensor, or an amp meter connected to the actuator.

In still other embodiments, means for delivering ultrasonic energy to the scraper blade 110 can assist with removal of tenaciously adhered particles or materials from the window 104 surface.

While illustrative embodiments have been illustrated and described, it will be appreciated that various changes can be made therein without departing from the spirit and scope of the invention.

The embodiments of the invention in which an exclusive property or privilege is claimed are defined as follows:

1. A scraper for an optical surface, comprising:
    a pivot shaft;
    a bracket, an axis thereof extending radially from the pivot shaft, with a blade slot formed along the axis;
    a rigid and non-deforming blade, having a length and a width that are significantly larger than a thickness thereof, the length and width defining a plane of the blade which remains perpendicular to the optical surface with one of the length edges arranged to bear against the optical surface and the other length edge mounted in the blade slot, the blade slot allowing rotation of the blade in the plane.

2. The scraper of claim 1, wherein the blade is configured to rotate about a pivot point that lies on the edge that bears against the optical surface.

3. The scraper of claim 1, wherein the edge that bears against the optical surface is formed by adjoining surfaces making an angle of 90 degrees or less.

4. The scraper of claim 1, wherein the blade includes a plurality of scraping edges.

5. The scraper of claim 1, wherein the blade is configured to oscillate.

6. The scraper of claim 1, wherein the blade edge that bears against the optical surface is made from a metal, ceramic, or rigid plastic.

7. The scraper of claim 1, wherein the slot includes a curved surface against which a matching curved surface of the other length edge of the blade seats.

8. The scraper of claim 1, wherein the slot includes a curved surface against which a matching curved surface on a proximal side of the blade seats.

9. A scraper for an optical surface, comprising:
    a bracket, with a blade slot formed along an axis of the bracket;
    a rigid and non-deforming blade, having a length and a width that are significantly larger than a thickness thereof, the length and width defining a plane of the blade which remains perpendicular to the optical surface with one of the length edges arranged to bear against the optical surface and the other length edge mounted in the blade slot the blade slot allowing rotation of the blade in the plane mounted in the blade slot in perpendicular relationship to the optical surface, against which an edge of the blade bears, the blade having limited rotation in the blade slot in a plane defined by the blade; and corresponding curved surfaces, a first of which is a proximal surface of the blade and a second of which is a surface of the slot, against which the first curved surface seats.

10. The scraper of claim 9, further comprising:
    a pivot shaft, a distal end of which is connected to the bracket.

11. A scraper for an optical surface, comprising:
    a pivot shaft, extending perpendicular to the optical surface and arranged for oscillatory rotation about an axis thereof;
    a bracket, an axis thereof extending radially from the pivot shaft;
    a blade slot extending along the axis of the bracket;
    a rigid and non-deforming blade, the blade having a length and a width that are significantly larger than a thickness thereof, the blade held in the blade slot such that the length and width define a plane of the blade which remains perpendicular to the optical surface with one of the length edges bearing against the optical surface and the other length edge mounted in the blade slot during the oscillatory rotation.

12. The scraper of claim 11, wherein the blade is configured to rotate about a pivot point that lies on the length edge that bears against the optical surface.

13. The scraper of claim 11, wherein the length edge that bears against the optical surface edge is formed by adjoining surfaces making an angle of 90 degrees or less.

14. The scraper of claim 11, wherein the blade includes a plurality of scraping edges.

15. The scraper of claim 11, wherein the blade is configured to oscillate.

16. The scraper of claim 11, wherein the length edge that bears against the optical surface bears is made from a metal, ceramic, or rigid plastic.

17. An instrument, comprising:
    an optical surface; and
    the scraper of claim 14, arranged in operative proximity to the optical surface.

18. The instrument of claim 17, wherein:
    the instrument is a particle analyzer.

19. The instrument of claim 17, wherein the instrument can analyze one or more of the size, shape, chemical composition, and concentration of particles.

* * * * *

UNITED STATES PATENT AND TRADEMARK OFFICE
CERTIFICATE OF CORRECTION

PATENT NO. : 8,468,642 B2
APPLICATION NO. : 12/404021
DATED : June 25, 2013
INVENTOR(S) : Becker et al.

It is certified that error appears in the above-identified patent and that said Letters Patent is hereby corrected as shown below:

In the Claims:

In column 7, line 43, please delete "blade slot the blade" and insert -- blade slot, the blade --.

Signed and Sealed this
Twenty-second Day of October, 2013

Teresa Stanek Rea
*Deputy Director of the United States Patent and Trademark Office*